(12) United States Patent
Ueno

(10) Patent No.: US 6,864,232 B1
(45) Date of Patent: Mar. 8, 2005

(54) AGENT FOR TREATING VISUAL CELL FUNCTION DISORDER

(75) Inventor: Ryuji Ueno, Potomac, MD (US)

(73) Assignee: Sucampo AG, Zug (CH)

( * ) Notice: Subject to any disclaimer, the term of this patent is extended or adjusted under 35 U.S.C. 154(b) by 0 days.

(21) Appl. No.: 09/869,129

(22) PCT Filed: Dec. 20, 1999

(86) PCT No.: PCT/JP99/07161

§ 371 (c)(1),
(2), (4) Date: Jun. 25, 2001

(87) PCT Pub. No.: WO00/38703

PCT Pub. Date: Jul. 6, 2000

Related U.S. Application Data

(60) Provisional application No. 60/113,939, filed on Dec. 24, 1998.

(51) Int. Cl.$^7$ ............................................. A61K 38/00
(52) U.S. Cl. .............................. 514/9; 514/21; 514/2; 536/6.5; 435/69.5
(58) Field of Search ................... 514/9, 21, 2; 536/6.5; 435/69.5

(56) References Cited

FOREIGN PATENT DOCUMENTS

| EP | 0 406 791 A2 | 1/1991 |
|---|---|---|
| EP | 0 532 862 | 3/1993 |
| EP | 0 532 862 A1 * | 3/1993 |
| RU | 2 084 222 C1 | 7/1997 |
| WO | WO 92/03049 | 3/1992 |
| WO | WO 94/13275 | 6/1994 |
| WO | WO 96/00073 | 1/1996 |
| WO | WO 99/00129 | 1/1999 |
| WO | WO 99/34830 | 7/1999 |
| WO | WO 00/09109 | 2/2000 |

OTHER PUBLICATIONS

Morice et al. 1993, J. of Biol. Chem, vol. 268, No. 5, pp. 3734–3738.*

Ryffel et al. 1995, Immunopharmacology, vol. 30, pp. 199–207.*

Tsuboi et al. 1994, Molecular Biology of the Cell, vol. 5, pp. 119–128.*

Nussenblatt R.B., Uveitis in Behcet's Disease. Int. Rev. Immunol. 1997, vol. 14, No. 1, pp. 67–79.*

J. Kiryu, et al., Annual Meeting of the Association for Research in Vision and Ophthalmology, vol. 39, No. 4, p. S273, "In Vivo Evaluation of the Inhibitory Effects of Tacrolimus (FK506) on Leukocyte Accumulation During Retinal Ischemia Reperfusion Injury", May 10–15, 1998.

M. Kikuchi, et al., Investigative Opthalmology and Visual Science, vol. 39, No. 7, pp. 1227–1232, "Protective Effects of FK506 Against Glutamate–Induced Neurotoxicity in Retinal Cell Culture", Jun. 1998.

A. Tsujikawa, et al., Stroke, vol. 29, No. 7, pp. 1431–1438, "Tacrolimus (FK506) Attenuates Leukocyte Accumulation After Transient Retinal Ischemia", 1998.

D. F. Martin, et al., The Journal of Immunology, vol. 154, No. 2, pp. 922–927. "Synergistic Effect of Rapamycin and Cyclosporin A in the Treatment of Experimental Autoimmune Uveoretinitis", 1995.

P. A. Pearson, et al., Investigative Ophthalmology & Visual Science, Annual Meeting of the Association for Research in Vision and Ophthalmology, vol. 35, No. 4, p. 1923, "Sustained Delivery of Cyclosporine (CsA) and Dexamethasone (DEX) in the Treatment of Experimental Proliferative Vitreoretinopathy", May 1–6, 1994.

G. Striph, et al., Arch. Ophthalmol., vol. 104, No. 1, pp. 114–117, "Retina S Antigen–Induced Uveitis. The Efficacy of Cyclosporine and Corticosteriods in Treatment", Jan. 1986.

M. Ishioka, et al., *American Journal of Ophthalmology*, vol. 118, pp. 723–729 (Dec. 1994).

D.A. Harkevich "Pharmacology", Moscow, "Meditsina", 1987, pp. 47–48.

"Opthamalic Diseases" by Prof. V.G. Kopaeva, M. "Meditsina", 2002, pp. 303–336.

U.S. Appl. No. 10/495,425, filed May 21, 2004, Ueno.

U.S. Appl. No. 09/869,129, filed Jun. 25, 2001, Ueno.

* cited by examiner

*Primary Examiner*—Christopher R. Tate
*Assistant Examiner*—B. Dell Chism
(74) *Attorney, Agent, or Firm*—Oblon, Spivak, McClelland, Maier & Neustadt, P.C.

(57) ABSTRACT

The present invention provides an agent for treating retinopathy containing a tricyclo compound of formula (I)

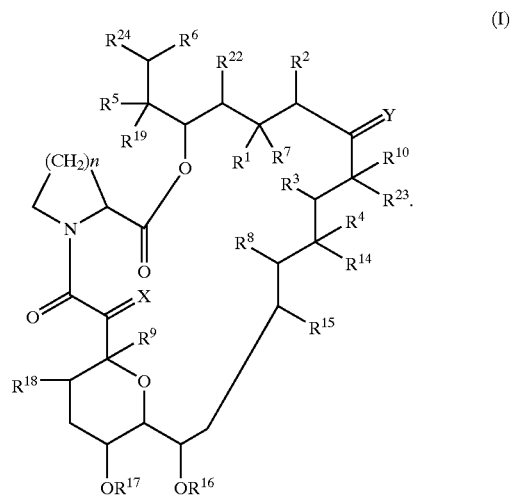

12 Claims, No Drawings

AGENT FOR TREATING VISUAL CELL FUNCTION DISORDER

This application is based on application No. 60/113,939 filed Dec. 24, 1998 in United States of America, the content of which is incorporated hereinto by reference.

TECHNICAL FIELD OF THE INVENTION

The present invention relates to an agent for treating visual cell function disorder.

BACKGROUND OF THE INVENTION

In the structure of the eye, the retina is present in the eyeground and controls the function of the eye to recognize the presence or absence and shape of an object by the presence of a visual cell layer of the retina. In recent years, patients with eye diseases undergo objective test of retinal function test by the determination of electroretinogram (hereinafter sometimes referred to merely as ERG). This determination is then utilized for the diagnosis of retinal conditions.

The ERG consists of an a-wave, a b-wave, a c-wave and the like. The a-wave is primarily reflects the function of visual cells, the b-wave reflects the function of the bipolar cell layer (mainly Müller cells) and the c-wave reflects the function of the retinal pigment epithelium. When the retinal function is damaged for some reason, it manifests in a change in the peak latency and amplitude of each wave. For example, in the case of diabetic retinopathy, the peak latency of each wave is extended from the early stage and the amplitude is attenuated; in degenerative disease of retina, such as pigmentary retinal degeneration, all waves are attenuated and disappear; and each wave becomes attenuated depending on the stages of disease in retinochoroidal disorders, such as central retinal artery occlusion, central retinal vein thrombosis, fundus hypertonicus, retinal detachment and the like.

While the b-wave originates from the source located more toward the central side of the retina than the visual cell from which the a-wave originates, when the light reaches the retina, the visual cell is first excited and the b-wave and the like are first generated when the excitement is transmitted to the retinal cells on the central side. Therefore, even when the source of origin is other than visual cell, the waves are under strong influence of the function of the visual cell. In other words, when the function of the visual cell is damaged, ERG components become abnormal even if the source of origin of the b-wave and the like is normal. Therefore, in ERG, the a-wave is the most important component, and if changes in peak latency and amplitude of a wave, which are caused by the damaged function of visual cell, can be suppressed or recovered the visual cell function disorder is expected to be effectively treated.

SUMMARY OF THE INVENTION

The present inventor has conducted intensive studies and surprisingly found that interleukin 2 (hereinafter sometimes referred to simply as IL-2) inhibitor has superior improving effect on visual cell function disorder and exhibit superior therapeutic effect on the diseases associated with visual cell function disorder, which resulted in the completion of the present invention.

Accordingly, the present invention provides the following.

(1) An agent for treating visual cell function disorder comprising an interleukin 2 inhibitor as an active ingredient.

(2) The agent of (1), wherein the interleukin 2 inhibitor is a macrolide compound or a cyclosporin.

(3) The agent of (2), wherein the macrolide compound is a tricyclo compound (1) of the following formula

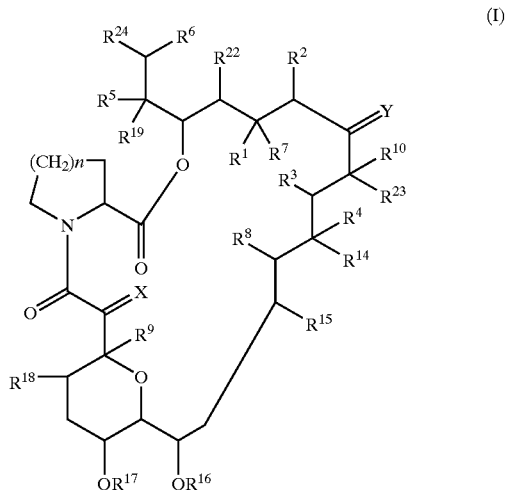

(I)

wherein adjacent pairs of $R^1$ and $R^2$, $R^3$ and $R^4$, and $R^5$ and $R^6$ each independently a) consist of two adjacent hydrogen atoms, wherein $R^2$ is optionally alkyl, or b) form another bond optionally between carbon atoms binding with the members of said pairs;

$R^7$ is hydrogen atom, hydroxy, protected hydroxy or alkyloxy, or may form oxo with $R^1$;

$R^8$ and $R^9$ are each independently a hydrogen atom or hydroxy $R^{10}$ is hydrogen atom, alkyl, alkyl substituted by one or more hydroxy, alkenyl, alkenyl substituted by one or more hydroxy or alkyl substituted by oxo;

X is oxo, (hydrogen atom, hydroxy), (hydrogen atom, hydrogen atom), or a group of the formula —$CH_2O$—;

Y is oxo, hydrogen atom, hydroxy), (hydrogen atom, hydrogen atom), or a group of the formula N—$NR^{11}R^{12}$ or N—$OR^{13}$;

$R^{11}$ and $R^{12}$ are each independently a hydrogen atom, alkyl, aryl or tosyl;

$R^{13}$, $R^{14}$, $R^{15}$, $R^{16}$, $R^{17}$, $R^{18}$, $R^{19}$, $R^{22}$ and $R^{23}$ are each independently a hydrogen atom or alkyl $R^{24}$ is an optionally substituted ring that may contain one or more hetero atom(s); and n is 1 or 2.

In addition to the meaning noted above, Y, $R^{10}$ and $R^{23}$ may be, together with the carbon atom they bind with, a saturated or unsaturated 5 or 6-membered heterocyclic group containing nitrogen atom, sulfur atom and/or oxygen atom, the heterocyclic group being optionally substituted by one or more group(s) selected from alkyl, hydroxy, alkyloxy, benzyl, a group of the formula —$CH_2Se(C_6H_5)$, and alkyl substituted by one or more hydroxy, or a pharmaceutically acceptable salt thereof.

(4) The agent of (2) or (3), wherein the macrolide compound is FK506.

(5) The agent of any of (1) to (4), which is used for the treatment of retinopathy.

(6) The agent of (5), wherein the retinopathy is ischemic retinopathy.

(7) The agent of (6), wherein the ischemic retinopathy is diabetic retinopathy.

(8) The agent of any of (1) to (7), which is in the form of a preparation for local administration to the eye.

(9) A method for treating visual cell function disorder, comprising administering an effective amount of an interleukin 2 inhibitor to a subject in need of the treatment of visual cell function disorder.

(10) Use of an interleukin 2 inhibitor for the production of a pharmaceutical composition for the treatment of visual cell function disorder.

DETAILED DESCRIPTION OF THE INVENTION

The IL-2 inhibitor to be used in the present invention is not particularly limited and may be any as long as it has an IL-2 inhibitory activity. One example thereof is an IL-2 production inhibitor. Another example is an IL-2 signal transduction inhibitor. Preferable examples thereof include macrolide compounds such as FK506, Ascomycin derivative, Rapamycin derivative and the like and cyclosporins and the like.

Specific examples of the macrolide compound include a tricyclo compound (I) of the following formula and a pharmaceutically acceptable salt thereof.

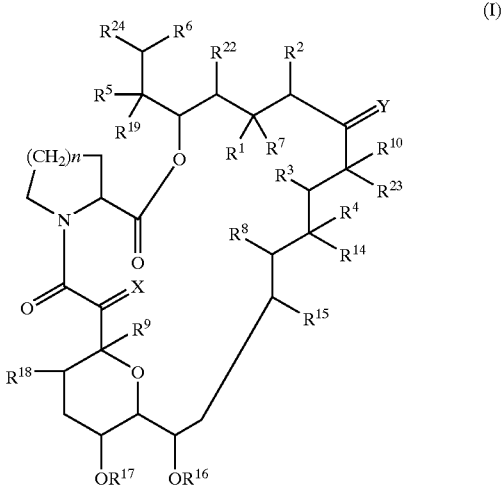

(I)

wherein adjacent pairs of $R^1$ and $R^2$, $R^3$ and $R^4$, and $R^5$ and $R^6$ each independently a) consist of two adjacent hydrogen atoms, wherein $R^2$ is optionally alkyl, or b) form another bond optionally between carbon atoms binding with the members of said pairs;

$R^7$ is hydrogen atom, hydroxy, protected hydroxy or alkyloxy, or may form oxo with $R^1$;

$R^8$ and $R^9$ are each independently a hydrogen atom or hydroxy;

$R^{10}$ is hydrogen atom, alkyl, alkyl substituted by one or more hydroxy, alkenyl, alkenyl substituted by one or more hydroxy or alkyl substituted by oxo;

X is oxo, (hydrogen atom, hydroxy), (hydrogen atom, hydrogen atom), or a group of the formula —CH$_2$O—;

Y is oxo, (hydrogen atom, hydroxy), (hydrogen atom, hydrogen atom), or a group of the formula N—NR$^{11}$R$^{12}$ or N—OR$^{13}$;

$R^{11}$ and $R^{12}$ are each independently a hydrogen atom, alkyl, aryl or tosyl $R^{13}$, $R^{14}$, $R^{15}$, $R^{16}$, $R^{17}$, $R^{18}$, $R^{19}$, $R^{22}$ and $R^{23}$ are each independently a hydrogen atom or alkyl $R^{24}$ is a optionally substituted ring that may contain one or more hetero atom(s); and n is 1 or 2.

In addition to the meaning noted above, Y, $R^{10}$ and $R^{23}$ may be, together with the carbon atom they bind with, a saturated or unsaturated 5 or 6-membered heterocyclic group containing nitrogen atom, sulfur atom and/or oxygen atom, wherein the heterocyclic group may be substituted by one or more group(s) selected from alkyl, hydroxy, alkyloxy, benzyl, a group of the formula —CH$_2$Se(C$_6$H$_5$), and alkyl substituted by one or more hydroxy.

Preferable $R^{24}$ is, for example, cyclo(C$_5$–C$_7$)alkyl optionally having suitable substituent, such as the following.

(a) 3,4-dioxocyclohexyl;

(b) 3-$R^{20}$-4-$R^{21}$-cyclohexyl, wherein $R^{20}$ is hydroxy, alkyloxy or —OCH$_2$OCH$_2$CH$_2$OCH$_3$, and $R^{21}$ is hydroxy, —OCN, alkyloxy, heteroaryloxy having suitable substituent, —OCH$_2$OCH$_2$CH$_2$OCH$_3$, protected hydroxy, chloro, bromo, iodo, aminooxalyloxy, azide, p-tolyloxythiocarbonyloxy, or $R^{25}R^{26}$CHCOO—(wherein $R^{25}$ is hydroxy optionally protected where desired or protected amino, and $R^{26}$ is hydrogen atom or methyl, or $R^{20}$ and $R^{21}$ in combination form an oxygen atom of epoxide ring); or (c) cyclopentyl wherein cyclopentyl is substituted by methoxymethyl, optionally protected hydroxymethyl where desired, acyloxymethyl (wherein acyl moiety is optionally quaternized dimethylamino or optionally esterified carboxy), one or more optionally protected amino and/or hydroxy, or aminooxalyloxymethyl. Preferable example includes 2-formyl-cyclopentyl.

The definition of each symbol used in the formula (I), specific examples thereof and preferable embodiments thereof are explained in detail in the following.

"Lower" means that a group has 1 to 6 carbon atoms unless otherwise indicated.

Preferable examples of the alkyl moiety of "alkyl" and "alkyloxy" include linear or branched fatty hydrocarbon residue, such as lower alkyl (e.g., methyl, ethyl, propyl, isopropyl, butyl, isobutyl, pentyl, neopentyl, hexyl and the like).

Preferable examples of "alkenyl" include linear or branched fatty hydrocarbon residue having one double bond, such as lower alkenyl (e.g., vinyl, propenyl (e.g., allyl and the like), butenyl, methylpropenyl, pentenyl, hexenyl and the like.

Preferable examples of "aryl" include phenyl, tolyl, xylyl, cumenyl, mesityl, naphthyl and the like.

Preferable examples of the protective group for "protected hydroxy" and "protected amino" include 1-(loweralkylthio) (lower)alkyl such as lower alkylthiomethyl (e.g., methylthiomethyl, ethylthiomethyl, propylthiomethyl, isopropylthiomethyl, butylthiomethyl, isobutylthiomethyl, hexylthiomethyl and the like), with more preference given to $C_1$–$C_4$ alkylthiomethyl and most preference given to methylthiomethyl;

tri-substituted silyl such as tri(lower)alkylsilyl (e.g., trimethylsilyl, triethylsilyl, tributylsilyl, tert-butyl dimethylsilyl, tri-tert-butylsilyl and the like), and lower alkyldiarylsilyl (e.g., methyldiphenylsilyl, ethyldiphenylsilyl, propyldiphenylsilyl, tert-butyldiphenylsilyl and the like, with more preference given to tri($C_1$–$C_4$)alkylsilyl and $C_1$–$C_4$ alkyldiphenyl-silyl, and most prefererence given to tert-butyl-dimethylsilyl, tert-butyldiphenylsilyl;

acyl such as fatty acyl derived from carboxylic acid, sulfonic acid and carbamic acid, fatty acyl substituted by aromatic acyl and aromatic, and the like.

The fatty acyl is exemplified by lower alkanoyl optionally having 1 or more suitable substituent(s) (e.g., carboxy) such as formyl, acetyl, propionyl, butyryl, isobutyryl, valeryl, isovaleryl, pivaloyl, hexanoyl, carboxyacetyl, carboxypropionyl, carboxybutyryl, carboxyhexanoyl and the like;

cyclo(lower)alkyloxy(lower)alkanoyl optionally having 1 or more suitable substituent(s) (e.g., lower alkyl) such as cyclopropyloxyacetyl, cyclobutyloxypropionyl, cyclo-heptyloxybutyryl, mentyloxyacetyl, mentyloxypropionyl, mentyloxybutyryl, mentyloxypentanoyl, mentyloxyhex-anoyl and the like, camphorsulfonyl;

lower alkylcarbamoyl having one or more suitable substituent(s) such as carboxy or protected carboxy and the like, such as carboxy(lower)alkylcarbamoyl (e.g., carboxymethylcarbamoyl, carboxyethylcarbamoyl, carboxypropylcarbamoyl, carboxybutylcarbamoyl, carboxypentylcarbamoyl, carboxyhexylcarbamoyl) and tri (lower)alkylsilyl(lower)alkyloxycarbonyl(lower) alkylcarbamoyl (e.g., trimethylsilylmethoxycarbonyl-ethylcarbamoyl, trimethylsilylethoxycarbonyl-propylcarbamoyl, triethylsilylethoxycarbonyl-propylcarbamoyl, tert-butyl dimethylsilylethoxy-carbonylpropylcarbamoyl, trimethylsilylpropoxy-carbonylbutylcarbamoyl).

Aromatic acyl is exemplified by aroyl optionally having suitable substituent(s) (e.g., nitro), such as benzoyl, toluoyl, xyloyl, naphthoyl, nitrobenzoyl, dinitrobenzoyl, nitronaph-thoyl and the like; and arenesulfonyl optionally having one or more suitable substituent(s) (e.g., halogen), such as benzenesulfonyl, toluenesulfonyl, xylenesulfonyl, naphthalenesulfonyl, fluorobenzenesulfonyl, chlorobenzenesulfonyl, bromobenzenesulfonyl, iodobenzenesulfonyl and the like.

The aliphatic acyl substituted by aromatic group may be, for example, ar(lower)alkanoyl optionally having one or more suitable substituent(s) (e.g., lower alkyloxy or trihalo (lower)alkyl and the like), wherein specific examples are phenylacetyl, phenylpropionyl, phenylbutyryl, 2-trifluoromethyl-2-methoxy-2-phenylacetyl, 2-ethyl-2-trifluoromethyl-2-phenylacetyl, 2-trifluoromethyl-2-propoxy-2-phenylacetyl and the like.

Of the above-mentioned acyl, more preferable acyl includes $C_1$–$C_4$ alkanoyl optionally having carboxy, cyclo ($C_5$–$C_6$)alkyloxy($C_1$–$C_4$)alkanoyl having two ($C_1$–$C_4$)alkyl in the cycloalkyl moiety, camphorsulfonyl, carboxy ($C_1$–$C_4$) alkylcarbamoyl, tri($C_1$–$C_4$)alkylsilyl($C_1$–$C_4$) alkyloxycarbonyl($C_1$–$C_4$)alkylcarbamoyl, benzoyl option-ally having 1 or 2 nitro groups, and benzenesulfonyl having halogen, phenyl($C_1$–$C_4$)alkanoyl having $C_1$–$C_4$ alkyloxy and trihalo($C_1$–$C_4$)alkyl. Of these, most preferred are acetyl, carboxypropionyl, mentyloxyacetyl, camphorsulfonyl, benzoyl, nitrobenzoyl, dinitrobenzoyl, iodobenzenesulfonyl, 2-trifluoromethyl-2-methoxy-2-phenylacetyl and the like.

Preferable examples of the "heterocyclic group consisting of saturated or unsaturated 5 or 6-membered ring having nitrogen atom, sulfur atom and/or oxygen atom" are pyrolyl, tetrahydrofuryl and the like.

The "heteroaryl optionally having a suitable substituent moiety" of the "heteroaryloxy optionally having a suitable substituent" is that exemplified for $R^1$ of the compound of the formula I of EP-A-532,088, with preference given to 1-hydroxyethylindol-5-yl. The disclosure is incorporated hereinto by reference.

The tricyclo compound (I) and a pharmaceutically accept-able salt thereof to be used in the present invention have superior IL-2 inhibitory action and immunosuppressive action, antibacterial action and other pharmacological activity, so that they are useful for the prophylaxis and treatment of rejection in organ or tissue transplantation, graft versus host reaction, autoimmune diseases, infectious dis-eases and the like, as noted, together with the production method thereof, in, for example, EP-A-184162, EP-A-323042, EP-A-423714, EP-A-427680, EP-A-465426, EP-A480623, EP-A-532088, EP-A-532089, EP-A-569337, EP-A-626385, WO89/05303, WO93/05058, WO96/31514, WO91/13889, WO91/19495, WO93/5059 and the like, all of these publications are hereby incorporated by reference.

In particular, the compounds called FR900506 (=FK506), FR900520 (Ascomycin), FR900523 and FR900525 are pro-duced by the genus *Streptomyces*, such as *Streptomyces tsukubaensis*, No. 9993 (depository: National Institute of Bioscience and Human-Technology Agency of Industrial Science and Technology, the Ministry of International Trade and Industry, 1–3, Higashi 1-chome, Tsukuba-shi, Ibaraki-ken, Japan (formerly: Fermentation Research Institute, Agency of Industrial Science and Technology, the Ministry of International Trade and Industry), date of deposit: Oct. 5, 1984, deposit number: FERM BP-927 or *Streptomyces hygroscopicus* subsp. *Yakushimaensis*, No. 7238 (depository: National Institute of Bioscience and Human-Technology Agency of Industrial Science and Technology, 1–3, Higashi 1-chome, Tsukuba-shi, Ibaraki-ken, Japan (formerly: Fermentation Research Institute, Agency of Industrial Science and Technology, the Ministry of International Trade and Industry), date of deposit: Jan. 12, 1985, deposit number: FERM BP-928 (EP-A-0184162), and the compound of the following formula, FK506 (general name: Tacrolimus) is a representative compound.

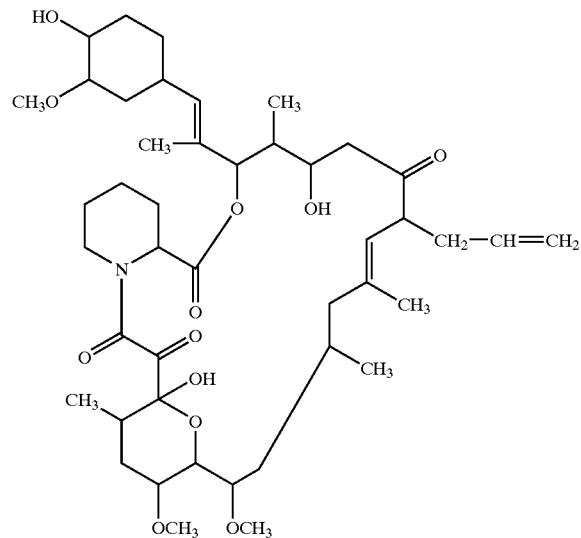

Chemical name: 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo [22.3.1.0$^{4.9}$]octacos-18-ene-2,3,10,16-tetraone Of the tricyclo compounds (I), more preferred is a com-pound wherein adjacent pairs of $R^3$ and $R^4$, and $R^5$ and $R^6$ each independently form another bond optionally between carbon atoms binding with the members of said pairs $R^8$ and $R^{23}$ each independently show hydrogen atom $R^9$ is hydroxy;

$R^{10}$ is methyl, ethyl, propyl or allyl;

X is (hydrogen atom, hydrogen atom) or oxo;

Y is oxo;

$R^{14}$, $R^{15}$, $R^{16}$, $R^{17}$, $R^{18}$, $R^{19}$ and $R^{22}$ each independently show methyl $R^{24}$ is 3-$R^{20}$-4-$R^{21}$-cyclohexyl,
wherein $R^{20}$ is hydroxy, alkyloxy or —OCH$_2$OCH$_2$CH$_2$OCH$_3$, and
$R^{20}$ is hydroxy, —OCN, alkyloxy, heteroaryloxy having suitable substituent, —OCH$_2$OCH$_2$CH$_2$OCH$_3$, protected hydroxy, chloro, bromo, iodo, aminooxalyloxy, azide, p-tolyloxythiocarbonyloxy or $R^{25}R^{26}$CHCOO— wherein $R^{25}$ is optionally protected hydroxy as desired, or protected amino, and $R^{26}$ is hydrogen atom or methyl), or $R^{20}$ and $R^{21}$ in combination form an oxygen atom of epoxide ring; and n is 1 or 2.

Particularly preferable tricyclo compound (I) include, besides FK506, Ascomycin derivatives such as halogenated derivative of 33-epi-chloro-33-desoxy Ascomycin described in Example 66a of EP-A-427,680 and the like.

Other preferable IL-2 inhibitors (macrolide compounds) include Rapamycin described in MERCK INDEX, 12 edition, No. 8288 and derivatives thereof. Preferable examples thereof include O-substituted derivative described at page 1 of WO95/16691, formula A, wherein the 40$^{th}$ hydroxy is —OR$_1$ (wherein R$_1$ is hydroxyalkyl, hydroalkyloxyalkyl, acylaminoalkyl and aminoalkyl), such as 40-O-(2-hydroxy)ethyl Rapamycin, 40-O-(3-hydroxy) propyl Rapamycin, 40-O-[2-(2-hydroxy)ethoxy]ethyl Rapamycin and 40-O-(2-acetaminoethyl)-Rapamycin. These O-substituted derivatives can be produced by reacting, under appropriate conditions, Rapamycin (or dihydro or deoxo Rapamycin) and an organic radical bound with leaving group (e.g., RX wherein R is an organic radical desirable as O-substituent, such as alkyl, allyl and benzyl moiety, and X is a leaving group such as CCl$_3$C(NH)O and CF$_3$SO$_3$)). The conditions are: when X is CCl$_3$C(NH)O, acidic or neutral conditions, such as in the presence of trifluoromethanesulfonic acid, camphorsulfonic acid, p-toluenesulfonic acid or their corresponding pyridinium or substituted pyridinium salt, and when X is CF$_3$SO$_3$, in the presence of a base such as pyridine, substituted pyridine, diisopropylethylamine and pentamethylpiperidine. The most preferable Rapamycin derivative is 40-O-(2-hydroxy)ethyl Rapamycin as disclosed in WO94/09010, which is hereby incorporated into the specification by reference.

The pharmaceutically acceptable salt of the tricyclo compound (1), Rapamycin and derivatives thereof are nontoxic and pharmaceutically acceptable conventional salts, which are exemplified by salts with inorganic or organic base such as alkali metal salt (e.g., sodium salt, potassium salt and the like), alkaline earth metal salt (e.g., calcium salt, magnesium salt and the like), ammonium salt, and amine salt (e.g., triethylamine salt, N-benzyl-N-methylamine salt and the like).

In the IL-2 inhibitor of the present invention, particularly macrolide compound, one or more pairs of stereoisomers, such as optical isomers and geometric isomers, may be included due to conformer or asymmetric carbon atom and double bond. Such conformers and isomers are also encompassed in the present invention. In addition, macrolide compounds can form solvates, which case is also encompassed in the present invention. Preferable solvate is exemplified by hydrates and ethanolates.

Other IL-2 inhibitors are known from MERCK INDEX, 12$^{th}$ ed., No. 2821, U.S. Pat. Nos. 4,117,118, 4,215,199, 4,288,431, 4,388,307, Helv. Chim. Acta, 60, 1568 (1977) and 65,1655 (1982) and Transplant. Proc. 17, 1362 (1985) and the like. Specifically, they are cyclosporins such as cyclosporin A, B, C, D, E, F and G and derivatives thereof. Particularly preferred is cyclosporin A. These are hereby incorporated into the specification by reference.

The tricyclo compound (I), pharmaceutically acceptable salt thereof, cyclosporins and derivatives thereof can be classified as "IL-2 production inhibitor" that inhibit production of IL-2. Rapamycin and derivative thereof can be classified as "IL-2 signal transduction inhibitor" that inhibit transmission of IL-2 signal.

In the present invention, visual cell function disorder means the state where visual cell of retina is suffering from disorder in the function for a certain reason, which can be specifically confirmed by the variation of peak latency or amplitude of a-wave in ERG as compared to those in the normal state. Inasmuch as the visual cell function disorder is caused by various retinal disorders such as degenerative retinopathy, retinochoroidal disorders and the like, the agent of the present invention for the treatment of visual cell function disorder can be used for treating retinopathy. In particular, the agent for treating visual cell function disorder of the present invention has superior action of improving visual cell function disorder, as is evident from the experimental example to be mentioned later, in ischemic retinopathy models, and can be used for the treatment of ischemic retinopathy. The ischemic retinopathy is caused by various reasons. For example, retinovascular diseases are caused by systemic disease, such as diabetes, hypertension and arteriosclerosis, and are exemplified by diabetic retinopathy, fundus hypertonicus, as well as local vascular disorders in retina, such as central retinal artery occlusion, central retinal vein thrombosis, retinal peripheral vascular occlusion, retinopathy of prematurity and the like.

The treatment in the context of the present invention includes any management such as prevention, treatment, alleviation of symptom, reduction of symptoms, prevention of progression and the like.

The interleukin 2 inhibitor to be used in the present invention can be used as a pharmaceutical agent for human and animals, and can be administered systemically or locally by oral administration, intravenous administration (inclusive of transfusion), subcutaneous administration, rectal or vaginal administration, administration to local site of the eye (inclusive of eye ointment). In consideration of systemic influence, significant expression of the effect and the like, it is particularly preferably used in the form for local administration to the eye.

The dose of the interleukin 2 inhibitor varies depending on the kind, age, body weight of the administration object such as human and animal, condition to be treated, desired therapeutic effect, administration route, treatment method, treatment period and the like. Generally, when it is administered systemically, the dose is about 0.0001–1000 mg, preferably 0.001–500 mg, which is given in a single dose or 2 to 4 doses a day or in a sustained manner. When it is administered locally to the eye, a preparation containing the active ingredient in a proportion of 0.001–10.0 w/v %, preferably 0.005–5.0 w/v %, is applied several times a day per eye, preferably instilled or applied 1 to 6 times a day.

According to the present invention, an interleukin 2 inhibitor, which is an active ingredient, can be administered alone or in combination with other pharmacologically active components. When administered after formulating a preparation, it can be administered as a preparation produced by a conventional method. The dosage form may be, for example, eye drop, eye ointment, powder, granule, tablet, capsule, injection, ointment and the like, with particular preference given to eye drop and eye ointment. Such preparation can be produced according to a conventional method. Of such preparations, an oral preparation is preferably a solid solution preparation produced in the same manner as in the preparation of EP-A-0240773. When an eye drop is desired, an eye drop as described in EP-A-0406791 is preferable. When desired, additives generally used for eye drop such as isotonizing agent (e.g., sodium chloride), buffer (e.g., boric acid, phosphoric acid-sodium hydrogen, sodium dihydrogenphosphate and the like), preservative (e.g., benzalkonium chloride, benzetonium chloride, chlorobutanol and the like), tackifier [e.g., sugar (lactose, mannitol, maltose sugar and the like), hyaluronic acid (sodium hyaluronate, potassium hyaluronate and the like), a salt thereof, mucopolysaccharide (chondroitin sulfate and the like), sodium polyacrylate, vinyl carboxy polymer, crosslinked polyacrylate, and the like] may be added. These are hereby incorporated into the specification by reference.

The present invention is explained in more detail in the following by way of Examples, to which the present invention is not limited.

EXAMPLES

Experimental Example 1

Effect on Changes in ERG of Rats with Retinal Ischemia

An ischemic state was induced by ligating the retinal blood vessel of rat and reperfusion to make ischemic retinopathy model in rat, with which the effect on changes in retinal potential was tested.

(1) Test Animal

Long Evans colored rats (male, 7- or 8-week-old when received: body weight 200–250 g) were prebred for 8 days and the animals free of abnormality in general conditions, such as body weight, were used for the test.

(2) Test Substance and Administration Method

As the active ingredient in the present invention, FK506 was used and the following 0.1% eye drop (suspension) was used as a test drug.

Test Drug

Suspension having the following composition which was prepared in the same manner as in EP-A-0406791 (Example 6)

| | |
|---|---|
| FK506 | 1.0 mg |
| polyvinyl alcohol | 7.0 mg |
| disodium hydrogenphosphate 12 hydrate | 0.05 mg |
| sodium dihydrogenphosphate 2 hydrate | 0.76 mg |
| phosphoric acid | appropriate amount |
| sodium hydroxide | appropriate amount |
| sodium chloride | 8.56 mg |
| benzalkonium chloride | 0.1 mg |
| injectable water | appropriate amount |
| Total amount | 1 ml |

As the control, the base agent of an eye drop without the active ingredient was used. The test drug was instilled to the eye by 10 μl/eye using a micropipette 3 times a day (8:00, 13:00, 18:00) from day 1 to day 7 of the test. The control agent was also administered by instillation in the same manner.

(1) Preparation of Ischemic Retinopathy Model

At day 8 of the test, the rats were anesthetized by intraperitoneal administration of diazepam (0.625 mg/kg), and pentobarbital (20 mg/kg) and a part of periorbita was removed from the side. A pedicle consisting of optic nerve, ophthalmic artery and ophthalmic vein was removed and the whole pedicle was ligated to cause ischemia. The ischemia was continued for 45 minutes and reperfused by releasing the ligation.

(2) ERG Determination

The apparatus and parameter were standarized by the following.

"Standard for Clinical Electroretinography" (International Standardization Committee)

Apparatus:

The Electrophysiologic Personal Interfaced Computer-2000 (LKC Technologies Incorporated)

ERG Determination Parameter:
- amplifier
  - high pass filter: 500 Hz
  - low pass filter: 0.3 Hz
  - notch filter: off
  - amplitude: 50 μV/division (maximum 1500 μV)
  - time: 20 ms/division (maximum 2500 ms)
- cornea electrode
  - impedance: 10 to 20 KΩ
- optical stimulation
  - single flash: 15 ms
  - intensity: 2.289 cd. s.m$^{-2}$
- ganzfeld
  - filter: none ERG was determined with the lapse of time before and after ischemia under the above-mentioned conditions.

(3) Results

Taking the ERG before ischemia as 100%, the ratio thereto of the peak latency of the a-wave after reperfusion was determined. It disappeared immediately after reperfusion. The results are shown in Table 1.

TABLE 1

| Administration group | (n) | a-wave peak latency (% average ± SD) | | |
|---|---|---|---|---|
| | | 60 min after reperfusion | 90 min after reperfusion | 120 min after reperfusion |
| Control drug | (8) | 195.6 ± 53.5 | 190.8 ± 55.3 | 191.9 ± 60.4 |
| Test drug | (8) | 137.1 ± 47.1* | 141.6 ± 44.8* | 134.4 ± 31.6* |

*$P < 0.05$ (comparison to control drug by ANOVA detection)

The a-wave peak latency disappeared immediately after reperfusion, but peak latency was prolonged with the lapse of time thereafter. As is evident from Table 1, the test drug administration group significantly suppressed the prolongation of the a-wave peak latency as compared to the control drug group.

What is claimed is:

1. A method for treating retinopathy, comprising administering to a subject in need thereof an effective amount of an agent comprising a tricyclo compound of formula (I)

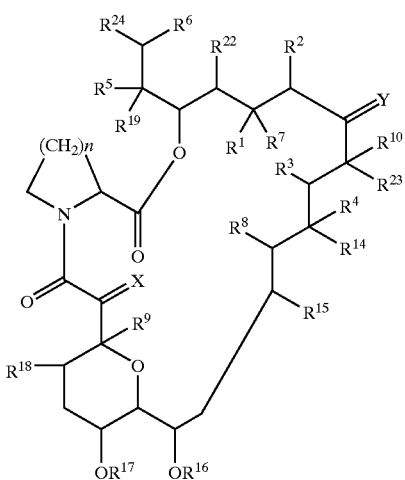

(I)

wherein adjacent pairs of $R^1$ and $R^2$, $R^3$ and $R^4$, and $R^5$ and $R^6$ each independently
 a) consist of two adjacent hydrogen atoms, wherein $R^2$ is optionally alkyl, or
 b) form another bond optionally between carbon atoms binding with the members of said pairs;
$R^7$ is hydrogen atom, hydroxy, protected hydroxy, or alkyloxy, or optionally form oxo with $R^1$;
$R^8$ and $R^9$ are each independently a hydrogen atom or hydroxy;
$R^{10}$ is hydrogen atom, alkyl, alkyl substituted by one or more hydroxy, alkenyl, alkenyl substituted by one or more hydroxy or alkyl substituted by oxo;
X is oxo, (hydrogen atom, hydroxy), (hydrogen atom, hydrogen atom), or a group of the formula —CH$_2$O—;
Y is oxo, (hydrogen atom, hydroxyl), (hydrogen atom, hydrogen atom), or a group of the formula N—NR$^{11}$R$^{12}$ or N—OR$^{13}$;
$R^{11}$ and $R^{12}$ are each independently a hydrogen atom, alkyl, aryrl or tosyl;
$R^{13}$, $R^{14}$, $R^{15}$, $R^{16}$, $R^{17}$, $R^{18}$, $R^{19}$, $R^{22}$ and $R^{23}$ are each independently a hydrogen atom or alkyl;
$R^{24}$ is a ring that is optionally substituted and optionally contain one or more hetero atom(s); and
n is 1 or 2,
wherein Y, $R^{10}$ and $R^{23}$ are optionally, together with the carbon atom they bind with, a saturated or unsaturated 5 or 6-membered heterocyclic group containing nitrogen atom, sulfur atom and/or oxygen atom, the heterocyclic group being optionally substituted by one or more group(s) selected from the group consisting of alkyl, hydroxy, alkyloxy, benzyl, a group of the formula —CH$_2$Se(C$_6$H$_5$), and alkyl substituted by one or more hydroxyl, or a pharmaceutically acceptable salt thereof.

2. The method of claim 1, wherein the tricyclo compound of formula (I) is

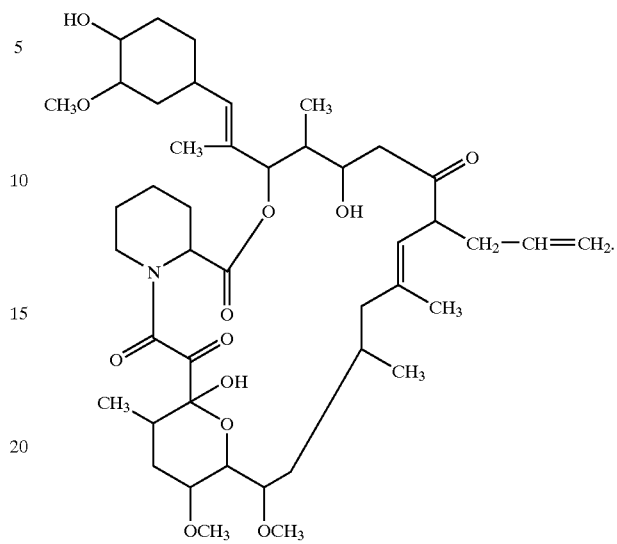

3. The method of claim 1, wherein the retinopathy is ischemic retinopathy.

4. The method of claim 3, wherein the ischemic retinopathy is selected from the group consisting of diabetic retinopathy, fundus hypertonicus, central retinal artery occlusion, central retinal vein thrombosis, retinal peripheral vascular occlusion and retinopathy of prematurity.

5. The method of claim 1, wherein said administering is by local administration to the eye.

6. The method of claim 5, wherein said effective amount comprises 0.001 to 10% weight per volume of the tricyclo compound of formula (I) administered 1 to 6 times per day.

7. The method of claim 6, wherein said effective amount comprises 0.005 to 5% weight per volume of the tricyclo compound of formula (I) administered 1 to 6 times per day.

8. The method of claim 1, wherein said effective amount is a dose ranging from 0.0001 to 1000 mg.

9. The method of claim 8, wherein said dose is administered 2 to 4 times per day.

10. The method of claim 1, wherein said effective amount is a dose ranging from 0.001 to 500 mg.

11. The method of claim 10, wherein said dose is administered 2 to 4 times per day.

12. The method of claim 1, wherein said agent further comprises one or more additives selected from the group consisting of an isotonizing agent, a buffer, a preservative, a tackifier, a hyaluronic acid or salt thereof, and a mucopolysaccharide.

* * * * *